United States Patent [19]

Stoltefuss et al.

[11] Patent Number: 4,540,684
[45] Date of Patent: Sep. 10, 1985

[54] 3-NITRO-5-AMIDE-1,4-DIHYDROPYRIDINES WITH POSITIVE INOTROPIC ACTIVITY

[75] Inventors: Jürgen Stoltefuss, Haan; Gerhard Franckowiak, Wuppertal; Horst Böshagen, Haan; Siegfried Goldmann, Wuppertal; Matthias Schramm, Cologne; Günter Thomas; Rainer Gross, both of Wuppertal, all of Fed. Rep. of Germany

[73] Assignee: Bayer Aktiengesellschaft, Leverkusen, Fed. Rep. of Germany

[21] Appl. No.: 612,093

[22] Filed: May 18, 1984

[30] Foreign Application Priority Data

Jun. 1, 1983 [DE] Fed. Rep. of Germany ....... 3319956

[51] Int. Cl.³ .................. C07D 211/98; C07D 405/12; A61K 31/70; A61K 31/455
[52] U.S. Cl. ........................................ 514/32; 514/43; 514/352; 546/309; 536/23; 536/17.3; 536/18.1
[58] Field of Search ................ 546/309, 321; 424/266; 536/23, 17.3, 18.1

[56] References Cited

U.S. PATENT DOCUMENTS 4,248,873 2/1981 Bossert et al. ....................... 546/271
4,285,955 8/1981 Wehinger et al. ................... 546/321

FOREIGN PATENT DOCUMENTS 3207982 10/1983 Fed. Rep. of Germany ....... 546/321

Primary Examiner—Henry R. Jiles
Assistant Examiner—Dale A. Bjorkman
Attorney, Agent, or Firm—Sprung Horn Kramer & Woods

[57] ABSTRACT

A 1,4-dihydropyridine derivative of the formula

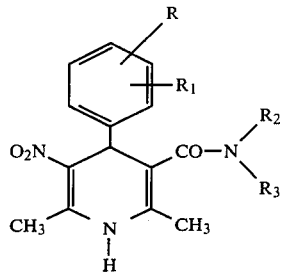

in which

R and $R_1$ each independently is hydrogen, $C_1$-$C_4$-alkyl, $C_1$ to $C_{12}$-alkoxy, $C_1$-$C_4$-halogenoalkoxy, halogen, nitro, trifluoromethyl,

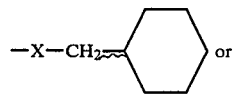

or

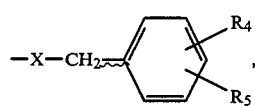

X is oxygen or sulphur, $R_4$ and $R_5$ each independently is hydrogen, $C_1$-$C_4$-alkyl, $C_1$-$C_6$-alkoxy, halogen, trifluoromethyl, amino or nitro, and $R_2$ and $R_3$ each independently is hydrogen, a $C_1$-$C_{10}$-alkyl, $C_2$-$C_{10}$-alkenyl or $C_3$-$C_{10}$-alkinyl radical which is optionally substituted by halogen, hydroxyl, $C_1$-$C_4$-alkoxy, amino, mono- and di-$C_1$-$C_4$-alkylamino, carbo-$C_1$-$C_6$-alkoxy and/or nitro, a $C_3$ to $C_6$-membered cycloalkyl radical, a phenyl radical which is optionally substituted by $C_1$-$C_4$-alkyl, $C_1$-$C_6$-alkoxy, halogen, amino and/or nitro, or a phenyl-$C_1$-$C_3$-alkyl radical, or a carbohydrate radical which is optionally bonded via a $C_1$-$C_8$-alkyl chain to the amide nitrogen atom or a pharmaceutically acceptable acid addition salt thereof, which improves the contractility of the heart, raises the blood pressure, lowers the blood sugar, reduces the swelling of mucous membranes and affects the salt and fluid balances of a patient.

13 Claims, No Drawings

3-NITRO-5-AMIDE-1,4-DIHYDROPYRIDINES WITH POSITIVE INOTROPIC ACTIVITY

The present invention relates to new 1,4-dihydropyridines, a process for their preparation and their use in medicaments, in particular in medicaments acting on the circulatory system and having positive inotropic effects.

It has already been disclosed that 1,4-dihydropyridines have vasodilator properties and can be used as coronary agents and antihypertensives (compare British Pat. No. 1,173,062; British Pat. No. 1,358,951; DE-OS (German Published Specification) No. 2,629,892 and DE-OS (German Published Specification) No. 2,752,820). It has also been disclosed that 1,4-dihydropyridines, being calcium antagonists, bring about depression of the contractility of smooth muscle and myocardium and can be employed for the treatment of coronary and vascular diseases (compare A. Fleckenstein, Ann. Rev. Pharmacol. Toxicol. 17, 149–166 (1977)).

Knowing these properties of the dihydropyridines, it could not have been foreseen that the compounds according to the invention from this class of substances do not have an action which depresses contractions, but have a positive inotropic effect on the mycardium which increases contractility.

The present invention relates to new 1,4-dihydropyridine derivatives of the general formula (I)

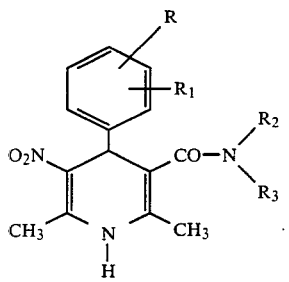

in which
R and $R_1$, which can be identical or different, represent hydrogen, $C_1$–$C_4$-alkyl, $C_1$ to $C_{12}$-alkoxy, $C_1$–$C_4$-halogenoalkoxy or halogen, nitro, trifluoromethyl or one of the groups

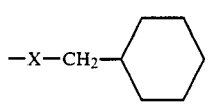

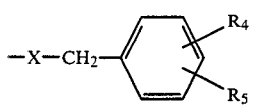

in which
X denotes oxygen or sulphur, and $R_4$ and $R_5$, which can be identical or different, denote hydrogen, $C_1$–$C_4$-alkyl, $C_1$–$C_6$-alkoxy, halogen, trifluoromethyl, amino or nitro, and $R_2$ and $R_3$, which can be identical or different, denote hydrogen, a $C_1$–$C_{10}$-alkyl, $C_2$–$C_{10}$-alkenyl or $C_3$–$C_{10}$-alkinyl radical which is optionally substituted by halogen, hydroxyl, $C_1$–$C_4$-alkoxy, amino, mono- and di-$C_1$–$C_4$-alkylamino, carbo-$C_1$–$C_6$-alkoxy or nitro, a $C_3$ to $C_6$-membered cycloalkyl radical, a phenyl radical which is optionally substituted by $C_1$–$C_6$-alkyl, $C_1$–$C_6$-alkoxy, halogen, amino or nitro or a phenyl-$C_1$–$C_4$-alkyl radical, or a carbohydrate radical which is optionally bonded via a $C_1$–$C_8$-alkyl chain to the amide nitrogen atom and their pharmaceutically acceptable acid addition salts.

Examples of salts which may be mentioned are: hydrochlorides, bisulphates, acetates, maleates, benzoates, citrates, tartrates or lactates.

The following are particularly suitable as the carbohydrate radical: monosaccharide radicals in the furanose and/or pyranose form and derivatives of 1-deoxynojirimycin. Particularly preferred radicals are 2-deoxy-D-glucose, glucosyl, the 1-deoxynojirimycin-1-methylene radical, 1-deoxynojirimycin-5-methylene radical and the N-(1-deoxynojirimycinylpropylene) radical.

The preferred compounds of the formula (I) are those in which
R represents hydrogen,
$R_1$ represents halogen, trifluoromethyl, nitro, hydrogen or one of the groups

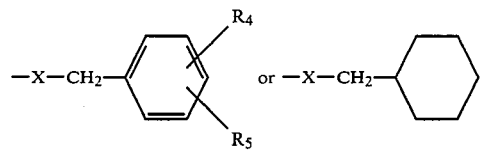

$R_4$ and $R_5$, which can be identical or different, denoting hydrogen, halogen or $C_1$–$C_4$-alkyl,
$R_2$ represents hydrogen or $C_1$–$C_4$-alkyl and
$R_3$ denotes hydrogen, $C_2$–$C_4$-alkenyl, $C_1$–$C_4$-alkyl which is optionally monosubstituted or polysubstituted by hydroxyl, $C_3$–$C_6$-cycloalkyl, di-$C_1$–$C_4$-alkylamino-$C_1$–$C_4$-alkyl, phenyl, $C_1$–$C_4$-alkyl substituted by phenyl, or a carbohydrate radical.

The dihydropyridines of the general formula (I) according to the invention can be prepared by (A) reacting amides of aminocrotonic acid of the general formula (II)

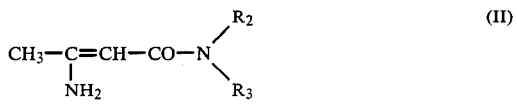

in which
$R_2$ and $R_3$ have the meaning indicated above, with aldehydes of the general formula (III)

in which
R and $R_1$ have the meaning indicated above, and nitroacetone

or (B) reacting benzaldehydes of the formula (III) and amides of acetoacetic acid of the formula (IV)

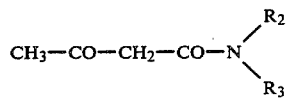 (IV)

in which $R_2$ and $R_3$ have the meaning indicated above, or their Knoevenagel condensation products of the formula (V)

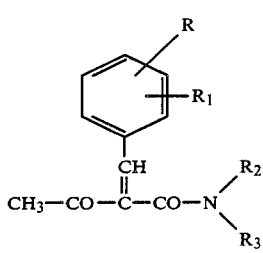 (V)

with an addition compound from nitroacetone and ammonia $CH_3-CO-CH_2-NO_2 \cdot NH_3$ or (C) by reacting dihydropyridines of the formula (VI)

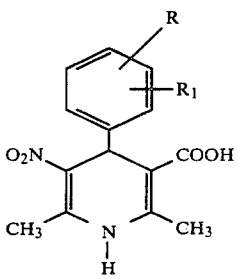 (VI)

in which

R and $R_1$ have the meaning indicated above, by methods known per se, with an amine or converting them into a reactive acid derivative and then reacting the latter with amines of the general formula (VII)

 (VII)

in which $R_2$ and $R_3$ have the meaning indicated above.

The following may be mentioned as examples of a reactive acid derivative: activated esters, hydroxysuccinimide esters, acid imidazolides, mixed anhydrides, and reaction products of the acids with dicyclohexylcarbodiimide.

When, for example, by process variant (A) the dimethylamide of β-aminocrotonic acid and 2-chlorobenzaldehyde are reacted with nitroacetone, then the reaction may be represented by the diagram below:

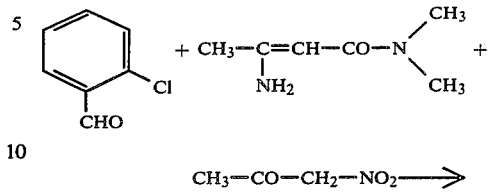

$CH_3-CO-CH_2-NO_2 \longrightarrow$

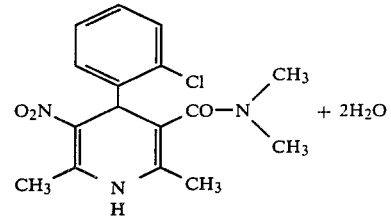 $+ 2H_2O$

When, for example, by process variant (B) the diethylamide of 2-trifluorobenzylideneacetoacetic acid is reacted with nitroacetone/ammonia, then the reaction can be represented by the diagram below:

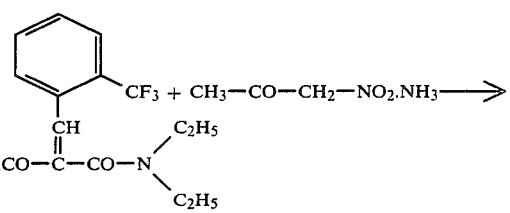

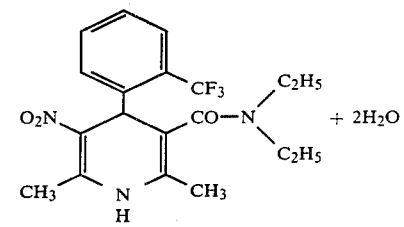 $+ 2H_2O$

When, for example, by process variant (C) 2,6-dimethyl-4-(2-(4-methylbenzyloxy)phenyl)-3-nitro-1,4-dihydropyridine-5-carboxylic acid is reacted with carbonyldiimidazole, and the resulting imidazolide is reacted with cyclopropylamine, then the reaction can be represented by the diagram below:

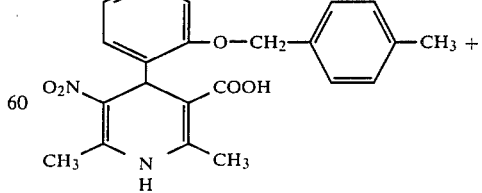

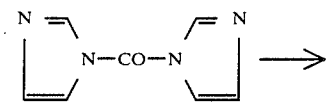 $\longrightarrow$

-continued

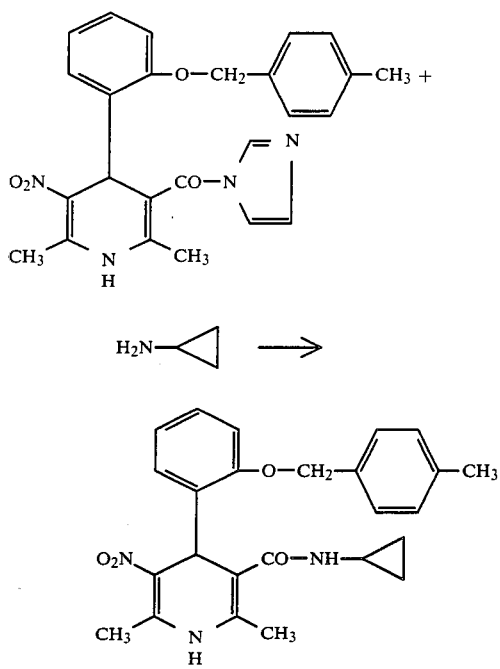

All inert organic solvents are suitable as the diluent for all process variants A, B and C. These preferably include alcohols, such as ethanol, methanol and isopropanol, ethers, such as dioxane, diethyl ether, tetrahydrofuran, glycol monomethyl ether and glycol dimethyl ether, or glacial acetic acid, dimethylformamide, dimethyl sulphoxide, acetonitrile, pyridine and hexamethylphosphoric triamide.

The reaction temperatures can be varied within a relatively wide range. In general, the process is carried out between 20° and 150° C., but preferably at the boiling point of the particular solvent.

It is possible to carry out the reaction under atmospheric pressure, but also under elevated pressure. In general, it is carried out under atmospheric pressure.

The abovementioned preparation processes are merely indicated for the purpose of clarification, and the preparation of the compounds of the formula (I) is not restricted to these processes but every modification of these processes can be used in the same manner for the preparation of the compounds according to the invention.

The ratio of amounts of the reactants to one another is arbitrary, in general equimolar amounts being employed. However, it has proved to be advantageous to use, in process A, nitroacetone in an up to 5 molar excess and, in process B, the nitroacetone/ammonia adduct in an up to 5 molar excess and, in process C, the amine of the formula VII in an excess of up to 10 moles.

Depending on the choice of the starting substances, the compounds according to the invention can exist in stereoisomeric forms which are related either as image and mirror image (enantiomers) or which are not related as image and mirror image (diastereomers). The present invention relates both to the antipodes and the racemic forms as well as to the mixtures of diastereomers. The racemic forms can, as can the diastereomers, be separated, in a known manner, into the homogeneous stereoisomeric components (compare, for example, E. L. Eliel, Stereochemistry of Carbon Compounds, Mc Graw Hill, 1962).

Aldehydes (III) used as starting materials are known and can be prepared by methods known from the literature (compare T. D. Harris and G. P. Roth, J. Org. Chem. 44, 146 (1979), German Offenlegungsschrift (German Published Specification) No. 2,165,260, German Offenlegungsschrift (German Published Specification) No. 2,401,665, Mijano et al., Chem. Abstr. 59, (1963), 13,929c, E. Adler And H.-D. Becker, Chem. Scand. 15, 849 (1961), E. P. Papadopoulos, M. Mardin and Ch. Issidoridis, J. Org. Chem. 31, 615 (1966), J. Am. chem. Soc. 78, 2543 (1956)).

Amides of aminocrotonic acid of the general formula (II) are either already known or can be prepared by known methods (see German Offenlegungsschrift (German Published Specification) No. 2,228,377).

Ylidene-β-carboxamides of the formula (V) which can be used according to the invention are either already known or can be prepared by known methods [Organic Reactions XV, 204 et seq. (1967)].

Dihydropyridine derivatives of the formula (VI) which can be used according to the invention are either known or can be prepared by known methods (see European Pat. No. 71,819).

Amines of the formula (VII) are known and they can be prepared by known methods (compare Houben-Weyl, Methoden der organischen Chemie (Methods of Organic Chemistry), volume 11/1; Paulsen, Angew. Chemie 78, 501–566 (1966); Le A 18 389=European Pat. No. 947).

In most cases, it is only with difficulty that carboxylic acids can be reacted with amines to give carboxamides directly. For this reason, reactive carboxylic acid derivatives are employed, carbonyl halides or carboxylic anhydrides in the simplest cases. The preparation of carboxamides under relatively mild conditions is possible by, for example, reacting the carboxylic acid with dicyclohexylcarbodiimide and amines in accordance with the following diagram

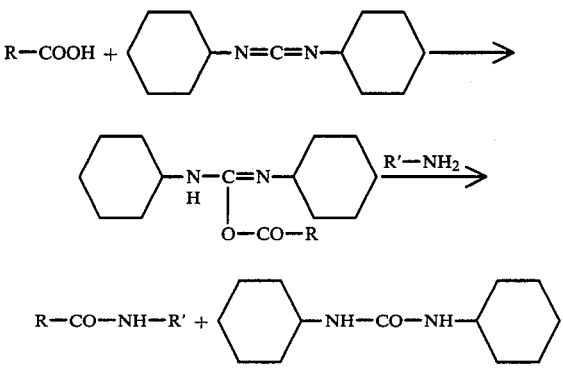

compare Fieser and Fieser, Reagents for Organic Synthesis, John Wiley & Sons, Inc. (1967), pages 231–36. J. C. Sheehan and G. P. Hess, J. Am. Chem. Soc. 77, 1067 (1955); U. Goodman and G. W. Kenner, Adv. in Protein Chem. 12, 488 (1957); W. A. Bonner and P. I. McNamee, J. Org. Chem. 26, 2554 (1961).

Examples of other activated carboxylic acid derivatives are hydroxysuccinimide esters of carboxylic acids, and imidazolides of carboxylic acids [Fieser and Fieser, Reagents for Organic Synthesis, John Wiley & Sons, Inc. 1967, pages 114–116; H. A. Staab, Angew. Chemie, Internat. Ed. 1, 351 (1962)]; N,N'-carbonyldi-s-triazine [Fieser and Fieser, Reagents for Organic Syntheses, John Wiley & Sons, Inc. 1967, page 116; H. C. Beyerman and W. U. Van den Brink, Rec. Trav. 80, 1372 (1961)], the list not being complete. (See also Methods for Amide Formation in: Survey of Organic Synthesis, Calvin A. Buehler and Donald E. Pearson, John Wiley & Sons, Volume 1 (1970) pages 895 et seq. and Volume 2 (1977)).

Nitroacetone can be prepared by known methods (compare N. Levy and C. W. Scarfe, J. Chem. Soc. (London) (1946) 1103 C. D. Hurd and M. E. Nilson, J. Org. Chem. 20 927 (1955)).

The new active compounds can be converted in a known manner into the customary formulations, such as tablets, capsules, coated tablets, pills, granules, aerosols, syrups, emulsions, suspensions and solutions, using inert, non-toxic, pharmaceutically suitable vehicles or solvents. The therapeutic reactive compound should, in each case, be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents and, for example, when using water as a diluent, organic solvents can optionally be used as auxiliary solvents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol), glycols (for example propylene glycol and polyethylene glycol), solid vehicles, such as, for example, natural rock powders (for example kaolins, aluminas, talc and chalk), synthetic rock powders (for example highly disperse silica and silicates), sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatine and the like. Furthermore, lubricants such as magnesium stearate, sodium lauryl sulphate and talc, can also be used when making tablets. In the case of aqueous suspensions and or elixirs which are intended for oral use, the active compounds can be mixed with various flavor-improving agents or colorants in addition to the abovementioned auxiliaries.

In the case of parenteral administration, solutions of the active compound, employing suitable liquid vehicles, can be used.

In general, it has proved advantageous, in the case of intravenous administration, to administer amounts of about 0.001 to 1 mg/kg, preferably about 0.01 to 0.5 mg kg, of body weight to achieve effective results, and in the case of oral administration, the dosage is about 0.01 to 20 mg/kg, preferably 0.1 to 10 mg/kg, of body weight.

Nevertheless, it can at times be necessary to deviate from the amounts mentioned, and in particular to do so as a function of the body weight of the experimental animal or of the nature of the administration method, but also because of the species of animal and its individual behavior toward the medicament, and the nature of the formulation of the medicament and the time or interval over which the administration takes place. Thus it can suffice in some cases to manage with less than the abovementioned minimum amount, whilst in other cases the upper limit mentioned must be exceeded. Where relatively large amounts are administered, it can be advisable to divide these into several individual administrations over the course of the day. The same dosage range is envisaged for administration in human medicine. In this connection, the above statements similarly apply.

The compounds according to the invention have a positive inotropic effect and thus exhibit a valuable spectrum of pharmacological effects which could not have been foreseen. They can be used as cardiotonics to improve the contractility of the heart. In addition, they can be employed as antihypotensives, to lower the blood sugar, to reduce the swelling of mucous membranes and to affect the salt and fluid balance.

The positive inotropic effect of the compounds of the formula (I) according to the invention is determined in the following design of experiment:

The left atria of guinea pig hearts are isolated and suspended in a thermostatted organ bath which contains an isotonic mineral salt solution, which is adjusted to be appropriate for the ionic medium and the pH of body fluids, and suitable nutrients. A gas mixture comprising oxygen and carbon dioxide is passed through this organ bath, the content of carbon dioxide being adjusted so that the pH of the organ bath remains constant. The left atria are tensioned in the organ bath and the tension is recorded by a force sensor, a particular basal tone being set up. Then the left atria are continuously subjected to electrical stimulation at set intervals, and the contractions which take place are recorded. After addition of the active compound, the contractions are again recorded. A strengthening in the contractions by at least 25% is regarded as a significant positive inotropic effect.

Thus, for example, the contractions of the left guinea pig atrium electrically stimulated at 1 Hz are strengthened by 38% by $10^{-6}$ g/ml of the compound from Example 8, by 43% by the compound from Example 9, and by 95% by the compound from Example 12, each likewise at a concentration of the particular compound of $10^{-6}$ g/ml.

PREPARATION EXAMPLES

Example 1

The dimethylamide of 1,4-dihydro-2,6-dimethyl-3-nitro-4-(2-benzyloxyphenyl)-5-carboxylic acid

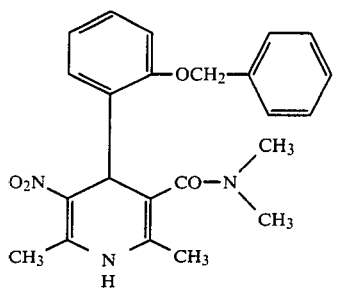

Process variant A 6.36 g (30 mmol) of 2-benzyloxybenzaldehyde are heated to reflux for 2 hours with 4.8 g (30 mmol) of the dimethylamide of β-aminocrotonic acid and 6.2 g (60 mmol) of nitroacetone in 45 ml of ethanol. The mixture is cooled and concentrated. The residue from evaporation is taken up in ethyl acetate, and the solution is washed with water, dilute sodium bicarbonate solution and again with water, dried and concentrated, whereupon crystallization occurs. The crystals are thoroughly stirred with ethanol, filtered off with suction and washed with ethanol. 1.6 g of a yellow-colored product of melting point 204°–206° C., with decomposition, are obtained.

Example 2

The cyclopropylamide of 1,4-dihydro-2,6-dimethyl-3-nitro-4-[2-(4-methylbenzyloxy)phenyl]-5-carboxylic acid

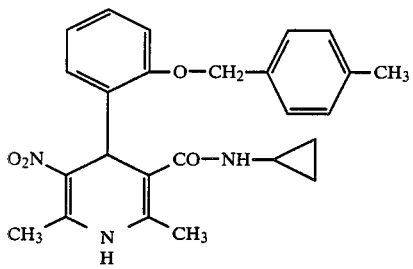

Process variant C

1. Preparation of the imidazolide of 1,4-dihydro-2,6-dimethyl-3-nitro-4-[2-(4-methylbenzyloxy)phenyl]-5-carboxylic acid 26 g (65.9 mmol) of 1,4-dihydro-2,6-dimethyl-3-nitro-4-[2-(4-methylbenzyloxy)phenyl]-5-carboxylic acid, of melting point 202° C. with decomposition, are suspended in 400 ml of absolute THF, and 12.9 g (79.6 mmol) of carbonyl-diimidazole are added, whereupon solution rapidly takes place. A further 6 g of carbonyl-diimidazole are added after 4 hours. The mixture is stirred for 18 hours and concentrated. The residue from evaporation is taken up in methylene chloride, and the solution is washed 2× rapidly with water, dried and concentrated. The residue from evaporation is crystallised by the addition of acetonitrile, and the crystals are filtered off with suction and washed with acetonitrile. 21.6 g (73.7% of theory) of the yellow-colored imidazolide, of melting point 193°–194° C., are obtained.

2. 4 g of the imidazolide of 1,4-dihydro-2,6-dimethyl-3-nitro-4-[2-(4-methylbenzyloxy)phenyl]-5-carboxylic acid in 40 ml of absolute tetrahydrofuran with 10 ml of cyclopropylamine are boiled to reflux for 20 hours. The mixture is cooled and concentrated. The residue from evaporation is taken up in ethyl acetate and extracted by shaking with 1N hydrochloric acid and water. The organic phase is dried and concentrated. The resulting residue from evaporation is dissolved in a little hot ethanol. After standing for several hours, the resulting crystals are filtered off with suction and washed with ethanol. 3.2 g of the cyclopropylamide of 1,4-dihydro-2,6-dimethyl-3-nitro-4-[2-(4-methylbenzyloxy)phenyl]-5-carboxylic acid, of melting point 198° C., are obtained.

The compounds prepared in analogy to process variant C are listed in the table below.

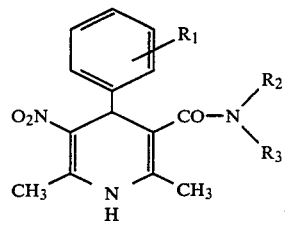

| Compound No. | Position | $R_1$ | $R_2$ | $R_3$ | Melting point °C. |
|---|---|---|---|---|---|
| 3 | 2 | —Cl | H | ◁ | 183–85 |
| 4 | 3 | Cl | H | —$_n$C$_4$H$_9$ | 223–24 |

-continued
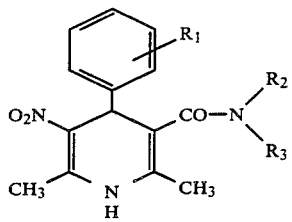
| Compound No. | Position | R₁ | R₂ | R₃ | Melting point °C. |
|---|---|---|---|---|---|
| 5 | 2 | —OCH₂—⌬—CH₃ | H | —ₙC₄H₉ | 203–04 |
| 6 | 2 | —O—CH₂—⌬ | H | ▷ (cyclopropyl) | 221 |
| 7 | 2 | —O—CH₂—⌬ | H | —CH₂—CH₂—OH | 192–93 |
| 8 | 2 | —O—CH₂—⌬ | H | —CH₂—CH=CH₂ | 186 |
| 9 | 2 | —O—CH₂—⌬ | H | —C(CH₃)₃ | 160 |
| 10 | 2 | —O—CH₂—⌬ | H | H | 230–31 |
| 11 | 2 | —OCH₂—⌬—F | H | H | 142 d |
| 12 | 2 | —O—CH₂—⌬—F | H | ▷ (cyclopropyl) | from 124 |
| 13 | 2 | —O—CH₂—⌬—F | H | —CH₂—CH₂—OH | 129–30 |
| 14 | 2 | —O—CH₂—⌬ | H | —CH₃ | 229 d |
| 15 | 2 | —O—CH₂—⌬—F | H | CH₃ | 203 |

-continued
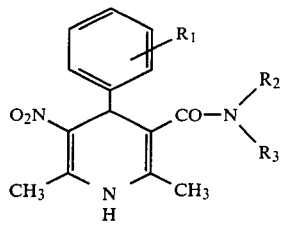
| Compound No. | Position | R₁ | R₂ | R₃ | Melting point °C. |
|---|---|---|---|---|---|
| 16 | 2 | —O—CH₂—C₆H₅ | H | C₂H₅ | 211–12 |
| 17 | 2 | —O—CH₂—C₆H₁₁ (cyclohexyl) | H | cyclopropyl | 191–93 |
| 18 | 2 | —O—CH₂—C₆H₅ | H | cyclohexyl | 210–11 |
| 19 | 2 | —O—CH₂—C₆H₄—F (3-F) | H | cyclopropyl | 221–23 |
| 20 | 2 | —O—CH₂—C₆H₄—F (3-F) | H | H | 138 d × 1 H₂O |
| 21 | 2 | —O—CH₂—C₆H₄—F (3-F) | H | CH₃ | 235 |
| 22 | 2 | —O—CH₂—C₆H₄—Cl (4-Cl) | H | H | 171–75 |
| 23 | 2 | —O—CH₂—C₆H₄—Cl (4-Cl) | H | CH₃ | 237 |
| 24 | 2 | —O—CH₂—C₆H₁₁ (cyclohexyl) | H | H | 218–20 |
| 25 | 2 | —O—CH₂—C₆H₄—Cl (4-Cl) | H | cyclopropyl | 147 |
| 26 | 2 | CF₃ | H | cyclopropyl | 253 d |

-continued
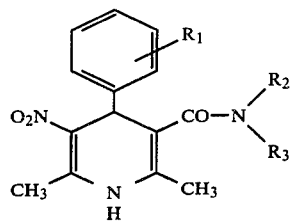
| Compound No. | Position | R₁ | R₂ | R₃ | Melting point °C. |
|---|---|---|---|---|---|
| 27 | 3 | NO₂ | H | –cyclopropyl | from 120 d |
| 28 | 2 | –S–CH₂–C₆H₄–F | H | –cyclopropyl | 167–70 |
| 29 | 2 | –O–CH₂–C₆H₄–CH₃ | H | H | 135 d |
| 30 | 2 | –O–CH₂–C₆H₄–CH₃ | H | –CH(CH₃)₂ | 222–24 |
| 31 | 2 | –O–CH₂–C₆H₄–CH₃ | H | –CH₂–CH₂–OH | 230–32 |
| 32 | 2 | –O–CH₂–C₆H₄–CH₃ | H | –C(CH₂OH)(CH₃)(CH₂OH) | 220–22 |
| 33 | 2 | –O–CH₂–C₆H₄–CH₃ | H | –C(CH₂OH)(CH₂OH)(CH₂OH) | 224 |
| 34 | 2 | –O–CH₂–C₆H₄–CH₃ | H | –CH₂–CH₂–N(C₂H₅)₂ | 156–158 |
| 35 | 2 | –O–CH₂–C₆H₄–CH₃ | H | –CH₂–CH₂–C₆H₅ | 210–12 |
| 36 | 2 | –O–CH₂–C₆H₄–CH₃ | H | –C₆H₅ | 259–60 |
| 37 |   | H | CH₃ | CH₃ | 244 |
| 38 |   | H | H | –C₆H₅ | 251–54 |

-continued

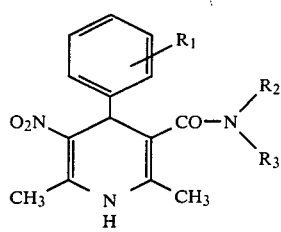

| Compound No. | Position | R₁ | R₂ | R₃ | Melting point °C. |
|---|---|---|---|---|---|
| 39 |  | H | H | cyclopropyl | 242 |
| 40 | 3 | —F | H | cyclopropyl | 250 |
| 41 | 2 | —F | H | cyclopropyl | 224–26 |
| 42 | 2 | —F | H | —CH₂—CH=CH₂ | 200 |
| 43 | 2 | O—CH₂—C₆H₄—CH₃ | H | —CH₂—CH=CH₂ | 232 |
| 44 | 2 | O—CH₂—C₆H₄—CH₃ | H | sugar moiety (HOH₂C, HO, HO, OH, CH₂—, NH) | 149–51 |
| 45 | 2 | O—CH₂—C₆H₄—CH₃ | H | sugar moiety (—H₂C, CH₂OH, HO, HO, OH, NH) | 242 |
| 46 | 3 | —NO₂ | H | sugar moiety (OH, HO, HO, OH, CH₂—, NH, H) | 160° C. |

The following were prepared in analogy to process variant A:

Example 47

The anilide of 1,4-dihydro-2,6-dimethyl-3-nitro-4-(2-trifluoromethylphenyl)-5-carboxylic acid, of melting point; 232° C.

Example 48

The diethylamide of 1,4-dihydro-2,6-dimethyl-3-nitro-4-(3-nitrophenyl)-5-carboxylic acid, of melting point: 197° C.

Example 49

The dimethylamide of 1,4-dihydro-2,6-dimethyl-3-nitro-4-(2-trifluoromethylphenyl)-5-carboxylic acid, of melting point; 218° C.

Example 50 (process variant B)

The dimethylamide of 1,4-dihydro-2,6-dimethyl-3-nitro-4-(2-benzyloxyphenyl)-5-carboxylic acid.

3.6 g (30 mmol) of nitroacetone-ammonia adduct (prepared from nitroacetone with an ethanolic solution of ammonia) are stirred with 2.6 g (20 mmol) of the dimethylamide of acetoacetic acid and 4.24 g (29 mmol) of 2-benzyloxybenzaldehyde in 30 ml of ethanol at 60° C. for 1 hour and then at the boiling point for 3 hours. The mixture is cooled and concentrated. The resulting residue from evaporation is separated on a column of length 25 cm and diameter 5 cm, which contains as the stationary phase silica gel 60 (Merck), 0.04–0.063 mm, and as the mobile phase toluene/ethyl acetate in the volume ratio 10:1. During the separation process, the mobile phase is changed stepwise to toluene/ethyl acetate in the volume ratio 1:1.

The fractions containing the almost pure product are combined and concentrated. 234 mg of an almost pure substance are obtained, and this is identical with the compound described in Preparation Example 1. The following compounds were also prepared by process variant C:

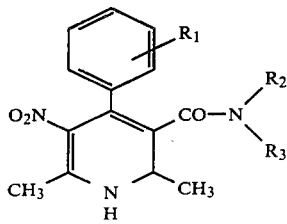

| Compound No. | Position | $R_1$ | $R_2$ | $R_3$ | Melting point °C. |
|---|---|---|---|---|---|
| 51 | 2 | —O—CH₂—⟨C₆H₄⟩—CH₃ | H | HO\,HO\,HO—(sugar)—N—(CH₂)₃—, OH | from 130 Rf = 0.325 |
| 52 | 2 | —O—CH₂—⟨C₆H₄⟩—CH₃ | H | —CH₂—CH₂—CH₂—OH | 211 |
| 53 | 2 | —O—CH₂—⟨C₆H₄⟩—CH₃ | H | —CH₂—CH(OH)—CH₂OH | 209–10 |
| 54 | 2 | —O—CH₂—⟨cyclohexyl⟩ | H | HO\,HO\,HO—(sugar)—N—(CH₂)₃—, OH | Rf = 0.385 |
| 55 | 2 | —O—CH₂—⟨C₆H₄⟩—Cl | H | HO\,HO\,HO—(sugar)—N—(CH₂)₃—, OH | Rf = 0.35 |
| 56 | 2 | —O—CH₂—⟨C₆H₄⟩ (F) | H | HO\,HO\,HO—(sugar)—N—(CH₂)₃—, OH | Rf = 0.305 |
| 57 | 2 | —O—CH₂—⟨Ph⟩ | H | —CH₂—CH(OH)—CH₂(OH) | 132° |
| 58 | 2 | —O—CH₂—⟨Ph⟩ | H | —CH₂—CH₂—CH₂—OH | 159–161° |
| 59 | 2 | —O—CH₂—⟨Ph⟩ | H | —CH₂—CH₂—CH₃ | 102° |

RfTLC Ready-coated plates (Merck) silica gel 60 F 254 Mobile phase: chloroform/methanol in the volume ratio 2:1

It will be understood that the specification and examples are illustrative but not limitative of the present invention and that other embodiments within the spirit and scope of the invention will suggest themselves to those skilled in the art.

We claim:

1. A 1,4-dihydropyridine derivative of the formula

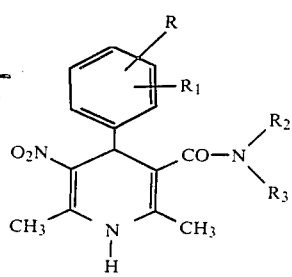

in which

R and $R_1$ each independently is hydrogen, $C_1$-$C_4$-alkyl, $C_1$ to $C_{12}$-alkoxy, $C_1$-$C_4$-halogenoalkoxy, halogen, nitro, trifluoromethyl,

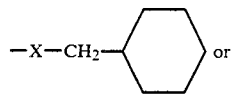 or

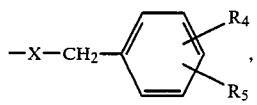

X is oxygen or sulphur, $R_4$ and $R_5$ each independently is hydrogen, $C_1$-$C_4$-alkyl, $C_1$-$C_6$-alkoxy, halogen, trifluoromethyl, amino or nitro, and $R_2$ and $R_3$ each independently is hydrogen, a $C_1$-$C_{10}$-alkyl, $C_2$-$C_{10}$-alkenyl or $C_3$-$C_{10}$-alkinyl radical which is optionally substituted by halogen, hydroxyl, $C_1$-$C_4$-alkoxy, amino, mono- and di-$C_1$-$C_4$-alkylamino, carbo-$C_1$-$C_6$-alkoxy and/or nitro, a $C_3$ to $C_6$-membered cycloalkyl radical, a phenyl radical which is optionally substituted by $C_1$-$C_4$-alkyl, $C_1$-$C_6$-alkoxy, halogen, amino and/or nitro, or a phenyl-$C_1$-$C_3$-alkyl radical, or a monosaccharide or 1-deoxynojirimycin radical which is optionally bonded via a $C_1$-$C_8$-alkyl chain to the amide nitrogen atom, or a pharmaceutically acceptable acid addition salt thereof, which exhibits positive inotropic activity.

2. A compound or salt according to claim 1, in which
R is hydrogen,
$R_1$ is halogen, trifluoromethyl, nitro, hydrogen,

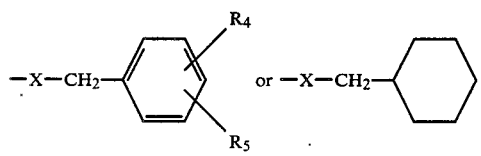

$R_4$ and $R_5$ each independently is hydrogen, halogen or $C_1$-$C_4$-alkyl,
$R_2$ is hydrogen or $C_1$-$C_4$-alkyl, and
$R_3$ is hydrogen, $C_2$-$C_4$-alkenyl, $C_1$-$C_4$-alkyl which is optionally substituted by hydroxyl, $C_3$-$C_6$-cycloalkyl, di-$C_1$-$C_4$-alkylamino-$C_1$-$C_4$-alkyl, phenyl, $C_1$-$C_4$-alkyl substituted by phenyl, or a monosaccharide or 1-deoxynojirimycin radical.

3. A compound according to claim 1, wherein such compound is the cyclopropylamide of 1,4-dihydro-2,6-dimethyl-3-nitro-4-[2-(4-methylbenzyloxy)phenyl]-5-carboxylic acid of the formula

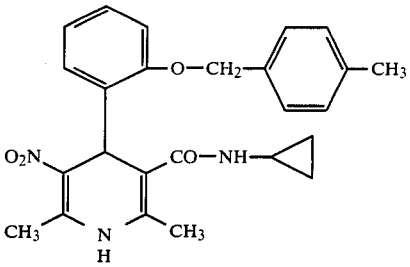

or a pharmaceutically acceptable acid addition salt thereof.

4. A compound according to claim 1, wherein such compound is the allylamide of 1,4-dihydro-2,6-dimethyl-3-nitro-4-(2-benzyloxyphenyl)-5-carboxylic acid of the formula

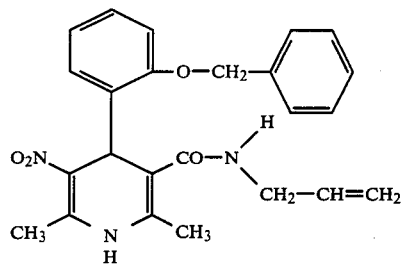

or a pharmaceutically acceptable acid addition salt thereof.

5. A compound according to claim 1, wherein such compound is the methylamide of 1,4-dihydro-2,6-dimethyl-3-nitro-4-[2-(4-fluorobenzyloxy)phenyl]-5-carboxylic acid of the formula

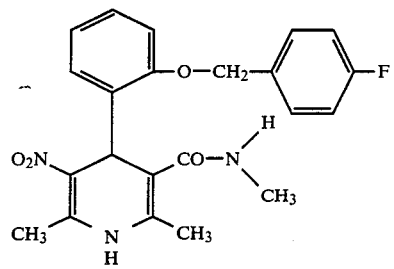

or a pharmaceutically acceptable acid addition salt thereof.

6. A compound according to claim 1, wherein such compound is the cyclopropylamide of 1,4-dihydro-2,6-dimethyl 3-nitro-4-(2-cyclohexylmethoxyphenyl)-5-carboxylic acid of the formula

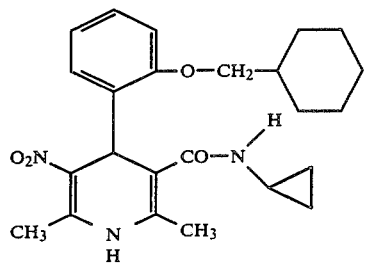

or a pharmaceutically acceptable acid addition salt thereof.

7. A compound according to claim 1, wherein such compound is the amide of 1,4-dihydro-2,6-dimethyl-3-nitro-4-[2-(4-chlorobenzyloxy)phenyl]-5-carboxylic acid of the formula

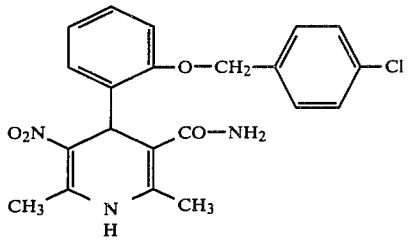

or a pharmaceutically acceptable acid addition salt thereof.

8. A compound according to claim 1, wherein such compound is the methylamide of 1,4-dihydro-2,6-dimethyl-3-nitro-4-[2-(4-chlorobenzyloxy)phenyl]-5-carboxylic acid of the formula

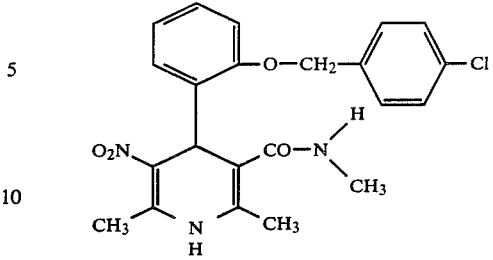

or a pharmaceutically acceptable acid addition salt thereof.

9. A pharmaceutical composition comprising a pharmaceutically acceptable diluent and an amount of a compound or salt according to claim 1 effective to improve the contractility of the heart, to raise the blood pressure, to lower the blood sugar, to reduce the swelling of mucous membranes, and to affect the salt and/or fluid balance.

10. A unit dose of a composition according to claim 9.

11. A composition according to claim 9 in the form of a tablet, capsule or ampule.

12. A method of improving the contractility of the heart, raising the blood pressure, lowering the blood sugar, reducing the swelling of mucous membranes and/or affecting the salt and/or fluid balance of a patient, comprising administering to such patient an amount effective for the intended purpose of a compound or salt according to claim 1.

13. The method according to claim 12, wherein such compound is
cyclopropylamide of 1,4-dihydro-2,6-dimethyl-3-nitro-4-[2-(4-methylbenzyloxy)phenyl]-5-carboxylic acid,
allylamide of 1,4-dihydro-2,6-dimethyl-3-nitro-4-(2-benzyloxyphenyl)-5-carboxylic acid,
methylamide of 1,4-dihydro-2,6-dimethyl-3-nitro-4-[2-(4-fluorobenzyloxy)phenyl]-5-carboxylic acid,
cyclopropylamide of 1,4-dihydro-2,6-dimethyl-3-nitro-4-(2-cyclohexylmethoxyphenyl)-5-carboxylic acid,
amide of 1,4-dihydro-2,6-dimethyl-3-nitro-4-[2-(4-chlorobenzyloxy)phenyl]-5-carboxylic acid or
methylamide of 1,4-dihydro-2,6-dimethyl-3-nitro-4-[2-(4-chlorobenzyloxy)phenyl]-5-carboxylic acid,
or a pharmaceutically acceptable acid addition salt thereof.

* * * * *

UNITED STATES PATENT AND TRADEMARK OFFICE
CERTIFICATE OF CORRECTION

PATENT NO. : 4,540,684

DATED : September 10, 1985

INVENTOR(S) : Stoltefuss et al.

It is certified that error appears in the above-identified patent and that said Letters Patent is hereby corrected as shown below:

Col. 19, line 14            Delete center of bottom structure and substitute:

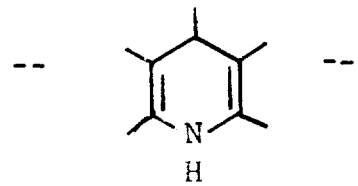

Signed and Sealed this

Twenty-first Day of January 1986

[SEAL]

Attest:

DONALD J. QUIGG

Attesting Officer        Commissioner of Patents and Trademarks